(12) United States Patent
De Kraker et al.

(10) Patent No.: US 9,304,119 B2
(45) Date of Patent: Apr. 5, 2016

(54) SYSTEM AND METHOD FOR TESTING ENGINE LUBRICANTS

(75) Inventors: Abraham Robert De Kraker, Sugar Land, TX (US); Brian Lee Papke, Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 320 days.

(21) Appl. No.: 13/599,897

(22) Filed: Aug. 30, 2012

(65) Prior Publication Data

US 2013/0230926 A1 Sep. 5, 2013

(51) Int. Cl.
*G01N 33/26* (2006.01)
*G01N 33/28* (2006.01)
*G01N 21/75* (2006.01)

(52) U.S. Cl.
CPC ............ *G01N 33/2888* (2013.01); *G01N 21/75* (2013.01)

(58) Field of Classification Search
CPC .............. G01N 33/2888; G01N 33/30; G01N 33/2835; G01N 31/22; F01M 11/10; G06F 17/30156; H04L 29/06; H04L 47/10
USPC .................... 73/19.11, 53.05, 114.55, 114.56, 73/114.57; 436/60; 422/82.05
See application file for complete search history.

(56) References Cited

U.S. PATENT DOCUMENTS

| | | | |
|---|---|---|---|
| 2,027,518 A | 1/1936 | Cornell et al. | |
| 3,990,960 A | 11/1976 | Ellison | 204/195 R |
| 4,057,999 A | 11/1977 | Bazika et al. | 73/53 |
| 4,082,511 A * | 4/1978 | Bedford | G01N 33/2876 436/60 |
| 5,071,527 A | 12/1991 | Kauffman | |
| 5,287,731 A * | 2/1994 | Florkowski | G01N 33/2805 422/53 |
| 5,313,824 A | 5/1994 | Herguth et al. | 73/53.05 |
| 5,401,661 A | 3/1995 | Florkowski et al. | 436/6 |
| 5,492,005 A | 2/1996 | Homan et al. | 73/61.62 |
| 5,569,842 A * | 10/1996 | Silvestri | G01N 21/3577 356/303 |
| 5,585,549 A | 12/1996 | Brevick et al. | |
| 5,693,874 A | 12/1997 | De La Cruz et al. | 73/61.62 |
| 5,707,871 A * | 1/1998 | Sadhir | G01N 33/2876 422/140 |
| 5,959,194 A | 9/1999 | Nenniger | 73/53.01 |
| 6,245,571 B1 * | 6/2001 | Roman | C10M 163/00 422/53 |
| D448,689 S | 10/2001 | Selby | D10/81 |
| 6,365,413 B1 | 4/2002 | Hall et al. | 436/60 |
| 6,370,946 B1 | 4/2002 | Lacey et al. | 73/61.62 |
| 6,405,582 B1 | 6/2002 | Boettcher | 73/61.72 |
| 6,459,995 B1 | 10/2002 | Collister | 702/23 |
| 6,464,011 B2 * | 10/2002 | Tubel | E21B 34/066 166/313 |
| 6,566,142 B1 | 5/2003 | Gateau et al. | 436/139 |
| 6,571,611 B2 | 6/2003 | Lacey et al. | 73/61.62 |

(Continued)

OTHER PUBLICATIONS

B.L. Papke et al.; "Surface Characterization of Model Lubricant-Derived Diesel Engine Piston Deposits," Journal of the Society of Tribologists and Lubrication Engineers, (May 1989), vol. 45, 9 pp. 575-585.

(Continued)

*Primary Examiner* — Peter Macchiarolo
*Assistant Examiner* — Mohammed Keramet-Amircolai

(57) ABSTRACT

Systems and methods for testing an engine lubricant are provided. The system includes a heated block having at least one cavity therein, at least one test cylinder receiving the engine lubricant therein, and at least one heated test piston selectively disposable into the engine lubricant of the test cylinder whereby deposits are formable on the test piston. The test cylinder is positionable in the cavity of the heated block and heatable thereby. Taxi oils and/or gases may be added to facilitate testing.

26 Claims, 8 Drawing Sheets

(56) References Cited

U.S. PATENT DOCUMENTS

| | | | |
|---|---|---|---|
| 6,739,184 B2 | 5/2004 | Brazeau et al. | 73/118.1 |
| 6,752,001 B1 | 6/2004 | La Pointe | |
| 6,789,413 B2 | 9/2004 | Brazeau et al. | 73/118.1 |
| 7,597,016 B2 | 10/2009 | Timmons et al. | 73/865.6 |
| 8,082,775 B2 | 12/2011 | Salisbury et al. | 73/114.55 |
| 2004/0216874 A1* | 11/2004 | Grant | E21B 49/10 166/264 |
| 2008/0090296 A1 | 4/2008 | Kinker et al. | |
| 2008/0202203 A1* | 8/2008 | Cummings | G01M 99/007 73/9 |
| 2009/0240640 A1* | 9/2009 | Blain | G01N 33/2888 706/12 |
| 2009/0249868 A1* | 10/2009 | Raichle | F02N 11/10 73/114.59 |
| 2012/0014407 A1 | 1/2012 | Anderson et al. | |
| 2012/0062894 A1* | 3/2012 | Micali | F01M 1/08 356/436 |

OTHER PUBLICATIONS

Brian L. Papke; "High Temperature Diesel Piston Deposit Formation: Wetting and Adhesion Phenomenon," Journal of the Society of Tribologists and Lubrication Engineers, (Feb. 15, 1991), vol. 48, 3, pp. 209-218.

PCT International Searching Authority Search Report dated Apr. 21, 2014, Ref. No. TH5348-PCT, Application No. PCT/US 13/57029 filed Aug. 28, 2013.

\* cited by examiner

SYSTEM AND METHOD FOR TESTING ENGINE LUBRICANTS

BACKGROUND

The present disclosure relates generally to testing operations. More specifically, the present disclosure relates to techniques for testing fluids, such as lubricants used in engines.

Lubricants may be used in machinery to prevent friction between moving parts, such as pistons and cylinders of an engine. In some cases, deposits may form in the lubricants that may hinder the movement of the parts and, therefore, impact the performance of the engine. Lubricants may be configured to reduce the likelihood of deposits and/or affect the performance of the engine.

Lubricants may include a mix of oils and other additives. The composition of the lubricant may be selected to define properties which can be used to enhance performance of the machinery. For example, various engines may specify the use of a certain viscosity of lubricant under certain conditions, such as outdoor temperature. In another example, the composition of the lubricant (and/or its additives) may be selected to control the engine's tendency to oxidize and form deposits.

Designed experiments may be performed to compare lubricants having various compositions. The experiments may involve performing tests of various lubricants to determine how each lubricant will perform in an engine. The experiments may be performed using apparatuses that simulate the engine and provide controlled conditions for testing. Examples of tests are provided in U.S. Pat. Nos. 5,313,824, 5,287,731, 7,597,016, 6,571,611, 6,566,142 and 5,492,005.

In some cases, experiments may be conducted to determine properties of different lubricants which may affect the performance of the machinery. For example, tests may be performed to determine oxidation of lubricants. Examples of oxidation tests include TFOUT (Thin-Film Oxygen Uptake Test), PDSC (Pressurized Differential Scanning calorimetry), (CVIT) Ciba Viscosity Increase Test, HOOT (Hot Oil Oxidation Test), FOAT (Ford Oil Aging Test), and Oxidator (Oronite Oxidation) test. Tests may also be performed to detect deposit formation. Examples of deposit tests include inclined plane, panel coker, hot tube, sliding ring, and micro-oxidation. Facilities used in performing the various tests may be configured to simulate environments in which the lubricants are used.

SUMMARY

In at least one aspect, the disclosure relates to a system for testing an engine lubricant. The system includes a heated block having at least one cavity therein, at least one test cylinder receiving the engine lubricant therein, and at least one heated test piston selectively disposable into the engine lubricant of the test cylinder whereby deposits are formable on the test piston. The cylinder is positionable in the cavity of the heated block and heatable thereby.

The system may further include a gas disposable into the test cylinder whereby oxidation of the engine lubricant is facilitated. The gas may include air, nitrogen dioxide and combinations thereof. The system may also include a motor for selectively moving the test piston in the test cylinder, a rod operatively connecting the motor to the piston, at least one controller operatively connectable to one of the gas source, the block heat source, the piston heat source and combinations thereof, a taxi oil mixable with the engine lubricant, a test hood, and a processor.

The system may also include at least one sensor. The sensor monitors at least one testing parameter selected from temperature, flow rate, position and combinations thereof.

In another aspect, the disclosure relates to a system for testing an engine lubricant including a heated block having at least one cavity therein, at least one test cylinder receiving the engine lubricant therein (the test cylinder positionable in the cavity of the heated block and heatable thereby), a taxi oil and a gas disposable in the test cylinder whereby oxidation of the engine lubricant is facilitated, and at least one heated test piston selectively disposable into the engine lubricant of the test cylinder whereby deposits are formable on the test piston.

Finally, in another aspect, the disclosure relates to a method for testing an engine lubricant. The method includes disposing the engine lubricant into at least one test cylinder, positioning the test cylinder into a cavity of at least one heated block, selectively disposing at least one heated test piston into the engine lubricant of the test cylinder, and examining the test piston for deposits. The method may also involve facilitating oxidation by disposing a gas into the test cylinder and/or disposing a taxi oil into the at least one test cylinder.

In another aspect, the disclosure relates to a system for testing an engine lubricant. The system includes a heated engine block having a cavity (the cavity receiving the engine lubricant therein), a heated tube block having a channel therethrough, and a tube disposable through the channel of the heated tube block. The tube has a lubricant end and a gas end. The lubricant end is positioned in the ending lubricant in the cavity. The gas end is in selective fluid communication with a gas source whereby one of gas and vacuum is selectively applied to the engine lubricant via the tube.

The heated engine block may have a temperature less than a temperature of the heated tube block. The gas source may include a gas or a vacuum. The gas may be air and/or nitrogen dioxide. The system may also include at least one valve operatively connectable to the gas source and the tube for selective application of the gas or the vacuum. The system may also include a controller operatively connectable to the valve for selective activation thereof. The tube may be a glass tube. The system may also include at least one heat coil selectively applying heat to the heated engine block and/or the heated tube block. The system may also include at least one controller operatively connectable to the heated engine block and/or the heated tube block and selectively controlling heat thereto. The system also includes a taxi oil mixable with the engine lubricant.

Finally in another aspect, the disclosure relates to a method for testing an engine lubricant. The method involves providing a test system including a heated engine block having a cavity therein, a heated tube block having a channel therethrough, and a tube disposable through the channel of the heated tube block (the tube having a lubricant end and a gas end). The method also involves disposing the engine lubricant into the cavity of the heated engine block, positioning a tube through a heated tube block, positioning a lubricant end of the tube into the engine lubricant in the heated engine block, selectively applying a gas or a vacuum to the test lubricant via the tube by selectively establishing fluid communication with a gas source, and examining the tube for deposits.

The selectively applying may involve applying gas to the test lubricant via the test tube or applying vacuum to the test lubricant via the test tube.

BRIEF DESCRIPTION OF THE DRAWINGS

So that the above recited features and advantages of the disclosure may be understood in detail, a more particular description of the disclosure, briefly summarized above, may be had by reference to the embodiments thereof that are illustrated in the appended drawings. It is to be noted, however, that the appended drawings illustrate only typical embodiments of this disclosure and are, therefore, not to be considered limiting of its scope. The figures are not necessarily to scale, and certain features and certain views of the figures may be shown exaggerated in scale or in schematic in the interest of clarity and conciseness.

DETAILED DESCRIPTION

The description that follows includes exemplary apparatuses, methods, techniques, and instruction sequences that embody techniques of the inventive subject matter. However, it is understood that the described embodiments may be practiced without these specific details.

The disclosure relates to techniques for testing lubricants, such as those used in engines. These techniques may involve the use of a simulated environment including an engine block with a test cylinder (or tube) and a heated piston selectively disposable into the test cylinder. The piston is selectively dipped into lubricant in the test cylinder for evaluating deposit formation on an engine piston. The lubricant may be a mix of a test oil, gases and/or used engine (or taxi) oil. The experiments may be performed over time and selectively controlled to provide the desired simulation.

Figure 1:
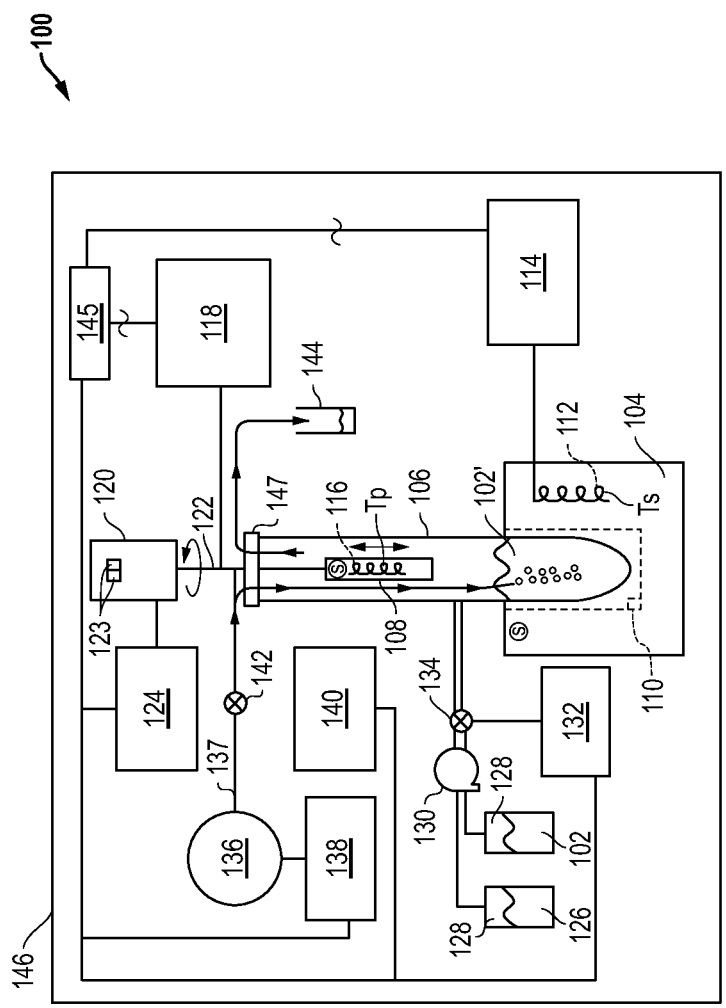
FIG. 1 is a schematic diagram depicting a system for testing engine lubricants in accordance with the present disclosure.

FIG. 1 illustrates a test system 100 usable for simulating an engine and evaluating a lubricant 102. The system 100 includes an engine block 104, a cylinder (or test tube) 106 and a piston 108. The cylinder 106 is supported in the engine block 104 and the piston 108 is selectively disposed into a lubricant mix 102' disposed in the cylinder 106. This configuration is intended to provide a simulated environment similar to that of an engine in which the lubricant 102 would be used.

The engine block 104 includes a cavity 110 for receiving and supporting the cylinder 106. The block 104 also has a heated coil 112 operatively connected to a block (or sump) temperature controller 114. The block 104 is selectively heated by the temperature controller 114. While the block 104 with a heated coil 112 and the block temperature controller 114 is depicted, any heat source may be provided and controlled as desired. The block 104 may be, for example, metal or ceramic for applying heat from the coil 112 to the cylinder 106.

The cylinder 106 is depicted as a transparent tube disposed in the block 104. The cylinder 106 may be, for example, glass (e.g., ASTM D943 glass oxidation tubes), to provide for visual monitoring of the test and/or controlled heating of the lubricant mix 102' therein. The cylinder 106 is also configured to receive the lubricant mix 102' and the piston 108. As shown, the cylinder 106 has an elongated shape (similar to a test tube) with a narrow opening to limit the input and output of items therein.

The cylinder 106 may receive any volume of the lubricant mix 102' (or related fluids). In a given example, the cylinder 106 receives about 350 ml of fluids. The lubricant mix 102' disposed in the cylinder 106 rests at the bottom of the cylinder 106. The lubricant mix 102' may be positioned in the cylinder 106 such that the portion of the cylinder 106 with the lubricant mix 102' therein is within the cavity 110 of block 104 for heating therein.

The piston 108 is movably positioned in the cylinder 106. The piston 108 may be, for example, a heated aluminum alloy having an elongated cylindrical shape deployable into the cylinder 106. The piston 108 has a coil 116 therein operatively connected to a piston temperature controller 118 and selectively heated thereby. As shown, the coil 116 is disposed within the piston 108 and heated by the temperature controller 118, but other configurations may be used to provide heat thereto. For example, the piston 108 may be independently heated by cartridge heaters or other heat sources.

The piston 106 is operatively connectable to a motor 120 and movable thereby. A rod 122 may operatively link the piston 108 to the motor 120 to facilitate movement of the piston 106. A timer (or controller) 124 may be provided to selectively activate the motor 120 to drive the piston 108. The timer 124 may be used, for example, to selectively deploy the piston 108 into the lubricant mix 102' for exposure thereto at a predetermined rate and for a predetermined time frame.

As indicated by the arrows, the piston 108 may be selectively moved in an axial and/or rotational motion. The motor 120 may provide a reciprocating action to the piston 106. The motor 120 may have, for example, gas solenoids 123 for driving the pistons. The solenoids 123 may be used to retract the piston 106 out of the lubricant mix 102' and then released to fall into the lubricant mix 102' using a gravity drop.

Figure 2:
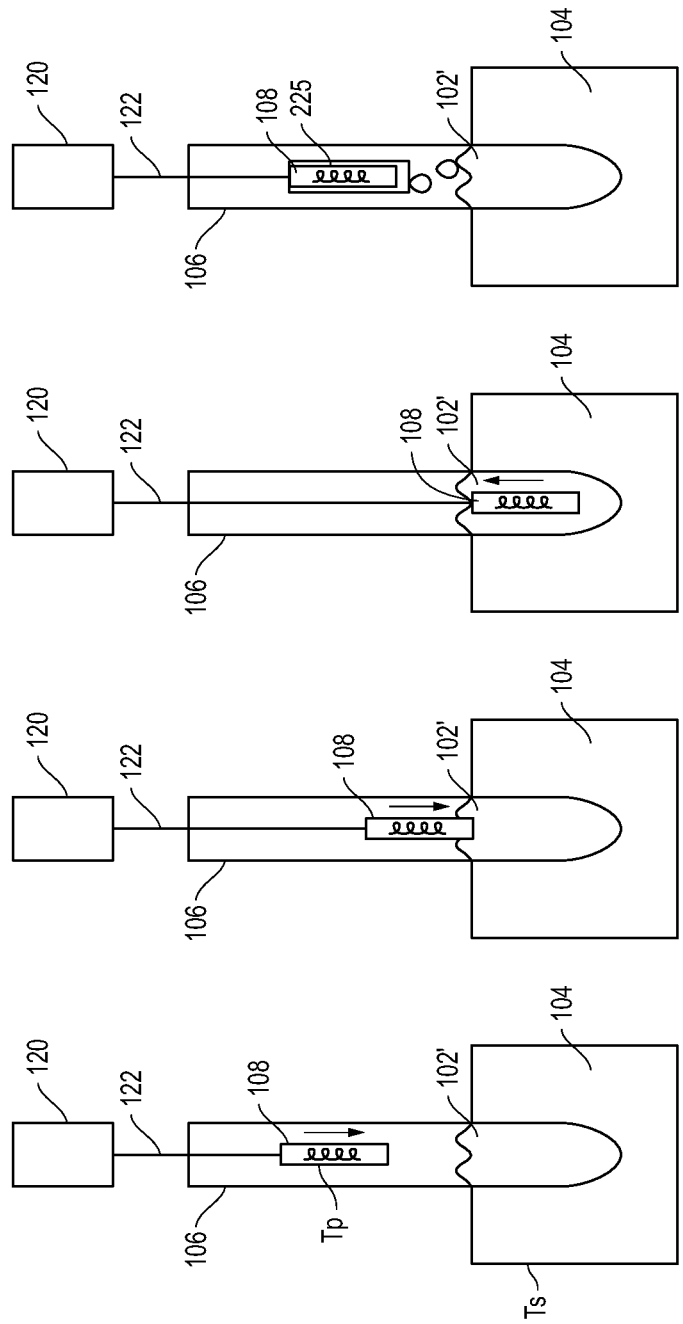
FIGS. 2A-2D are schematic diagrams depicting a testing cycle performed using the system of FIG. 1 in accordance with the present disclosure.

FIGS. 2A-2D depict movement of the piston 108 during a testing cycle. The piston 108 may be selectively deployed to a submerged position in the lubricant mix 102' by a rod 122 in a controlled sequence. The piston 108 may be released from a retracted position above the lubricant mix 102' as shown in FIG. 2A, to gravitationally drop to a contact position with the lubricant mix 102' as shown in FIG. 2B, and on to a submerged position as shown in FIG. 2C. After exposure to the lubricant mix 102', the piston 108 may be retracted to a non-submerged position above the lubricant mix 102' using the motor 120 as shown in FIG. 2D. In the retracted position, the lubricant mix 102' may fall back into the cylinder 108 leaving a film 225 of the lubricant mix 102' on the piston 108. The piston 108 may then be removed and examined for the formation of deposits thereon.

The test time and sequence may be adjusted as desired to achieve the desired test and/or to simulate operating conditions. By way of example, variable cycle times for a given sequence may be provided from about 10 seconds to several minutes. During the cycle, the temperature $T_P$ of the piston 108 and the temperature $T_B$ of the block 104 may be controlled by the temperature controllers 114 and 118 (see FIG. 1A), respectively, to achieve the desired test sequence. Selected temperatures of the piston 108 and the block 104 may be predefined, for example, to about 320 C. The temperature of the piston 108 and the block 104 may be selectively adjusted as will be described more fully herein.

Referring back to FIG. 1, the cylinder 106 may also be provided with various fluids to alter the testing conditions. For example, a test lubricant 102 may be mixed with a taxi oil 126 to form test lubricant mix 102'. The taxi oil 126 may be a lubricant that may be similar to the test lubricant 102, but having previously been processed (or used). The taxi oil 126 may be used, for example, to increase the speed of the test.

The test lubricant 102 may be any lubricant (e.g., motor oil) or mix of lubricants to be tested. A mixture of lubricants may include the test lubricant 102 and another lubricant, such as a taxi oil. A taxi oil refers to lubricants that have been previously used over a period of time, for example, in a taxi cab. The taxi oil may be added in desired ratios with the test lubricant to speed up the oxidation and/or the test process. Gas (e.g., air or NO2) may also be added to the fluid to facilitate oxidation and/or testing. Other lubricants, gases and/or additives may also be provided as desired to achieve the desired test conditions for evaluating the test lubricant 102.

One or more fluids, such as the taxi oil 126 and test lubricant 102, may be contained in containers 128 and deployed into the cylinder 106 for testing. As shown, a pump 130, controller 132 and valve 134 may be provided to manipulate flow of the fluids (e.g., taxi oil 126 and/or lubricant 102) in desired amounts to form the lubricant mix 102'. In a given example, the lubricant mix 102' may include a 50:50 mixture of lubricant 102 with a used engine lubricant (e.g., ca. 6K of an NYC taxi oil). In another example, the lubricant mix 102' may include, for example, 60% taxi oil 126 and 40% test lubricant 102. A desired amount of taxi oil 126 may be provided to facilitate the testing process while still permitting the test lubricant 102 to be evaluated. The lubricant mix 102' may also include various combinations of a pre-aged, new or used blend of test lubricant 102 and taxi oil 126.

Gas 136 may be inserted into the cylinder 106. The gas 136 may be configured to simulate exhaust gases for exposure to the heated lubricant mix 102'. The gas 136 may include one or more gases injectable into the cylinder 106 to facilitate testing. The gas 136 may be, for example, air, nitrogen dioxide or other gases that may facilitate oxidation of the lubricant mix 102'.

By way of example, gas sparging may include a mix of dry air or a mix of air with $NO_2$, with the mixture being in the amount of about 200 cc/min or from about 10 cc/min to about 200 cc/min. A mixture of air and $NO_2$ gas may be contained in a gas cylinder with about 3000 ppm of $NO_2$. Gas blending systems may optionally be used to mix dry compressed air with custom concentrations of $NO_2$ (e.g., from about 250 to about 400 ppm of $NO_2$).

The gas 136 may be deployed into the cylinder 106 via a flowline 137 and used to form bubbles in the lubricant mix 102' as shown. Safety controls 138 may be provided to monitor the gas 136 and prevent unexpected release, for example when using noxious gases. The flow controller 140 and valve 142 may also be provided to control mixing and/or release of gas 136 into the cylinder 106. Gas blending may be controlled by a mass control flowmeter or flow controller 140 using, for example, 'feed-back' loop and 'surge' tank mixing.

A gas collector 144 may optionally be provided for capturing volatile lubricant components (or volatiles) released from the cylinder 106. The cylinder 106 may be provided with a lid 147 to seal gases in the cylinder 106. A flowline may be provided through the lid 147 and to the gas collector 144 for collection of volatiles from the cylinder 106. The volatiles collected may be measured, monitored, evaluated or otherwise examined.

The system 100 may also be provided with other features to facilitate testing. For example, a vent hood 146 may be provided to house the system 100. Various components may be housed in the vent hood 146. By way of example, some components, such as the controllers may be positioned outside the vent hood 146.

The system 100 may also be provided with a processor (and/or controller) 145 for operating the system 100. The processor may be operatively connected to various components, such as the sump temperature controller 114 and the piston temperature controller 118 to control heat of the block 104 and/or the piston 108. The block 104 and/or piston 108 may be set at a given predefined temperature which may be the same as or different from each other. The block 104 and piston 108 may be selectively heated separately or in combination to achieve the desired heating of the lubricant mix 102'. By way of example, the temperature of the lubricant mix 102' may be heated using the heated block 104 and/or heated piston 108 to, for example, 155 C or in a temperature range of from about 100 C to about 200 C.

The timer 124 may also be operatively connected to the processor 145 to control operation of the piston 108 and the sequence of the test cycle (e.g., as in FIGS. 2A-2D). Other components of the system 100 (e.g., safety controller 138, flow controller 140, pump controller 132), may be operatively connected to the processor 145 for data communication and/or operative control.

Sensors S may be positioned about the system 100 and operatively connected to the processor 145 for providing data concerning various aspects of the test. As shown, sensors are in piston 108 and block 104, but could be at any location to collect data as desired. Data from the sensors S may be used as an input to determine operation of various components, such as flow rates of gas 136, taxi oil 126 and/or lubricant 102 into the cylinder 106. The processor may be used to manipulate operation based on predetermined criteria or in response to testing conditions.

In operation, the system 100 may be used to perform a test on one or more test lubricants 102. Deposit tendencies of one or more lubricants may be tested simultaneously. Multiple test series may be performed over a given period depending on the cycle times and capacity for the pistons 106. The cycle of the tests of one or more of the cylinders may be controlled and selectively performed to provide variations in test results and to compare various lubricant compositions.

In an example test, the system 100 performs a test with the lubricant mix maintained at 155 C with an input of 200 cc/min of gas including a mixture of air with 400 ppm $NO_2$. In this case, the block coil 112 is activated by sump temperature controller 114, but the piston coil 116 remains off. Deposits formed in about 15 hours. In another case with a lubricant mix 102' at 155 C, 100 cc/min of air mixed with 400 ppm NO2, a piston temperature of 320 C and a piston movement of 1 cycle/min, deposits were formed on the piston in about 7 hours.

Figure 3:
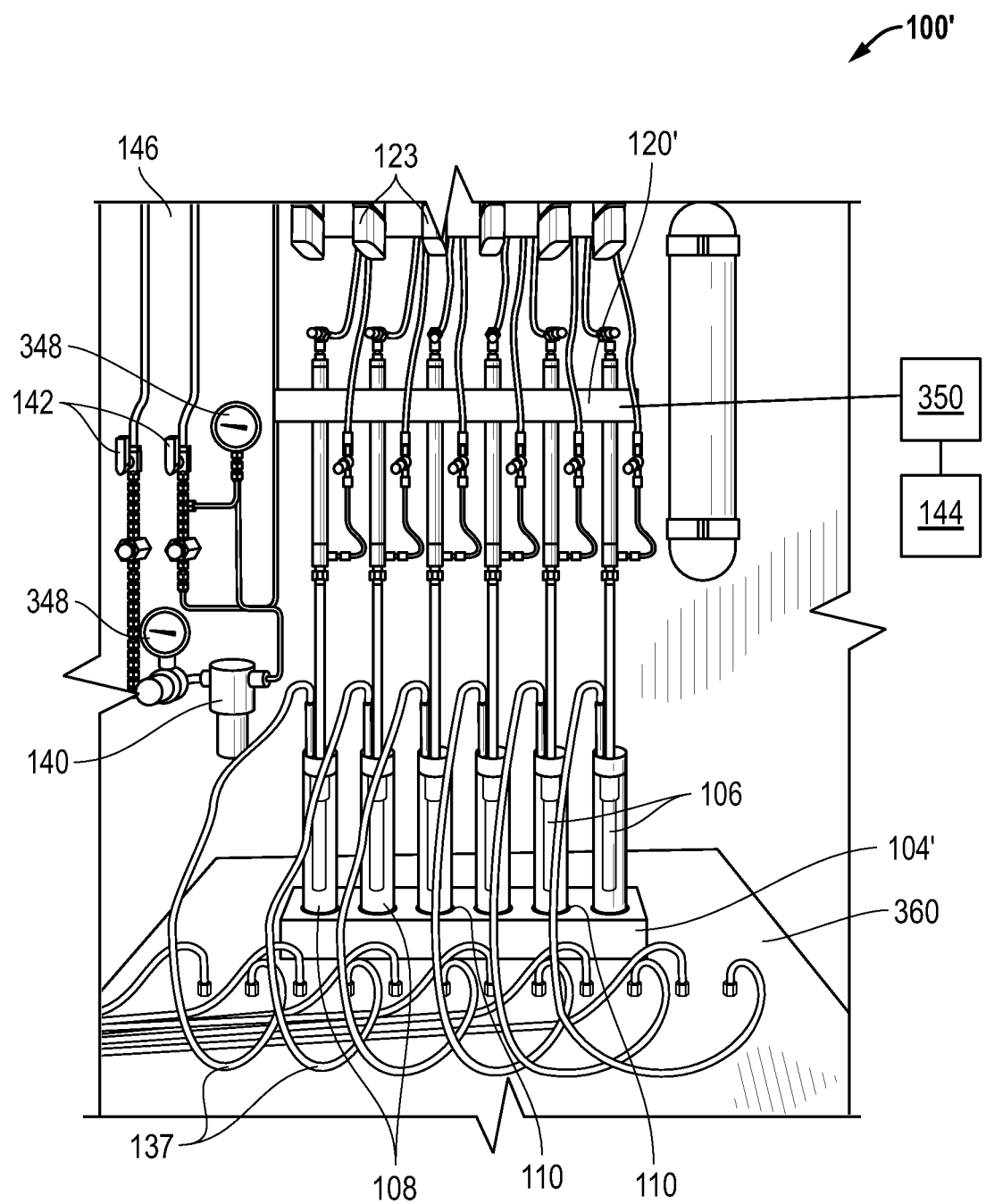
FIG. 3 is a schematic diagram depicting a multi-cylinder system for testing engine lubricants in accordance with the present disclosure.
Figure 4:
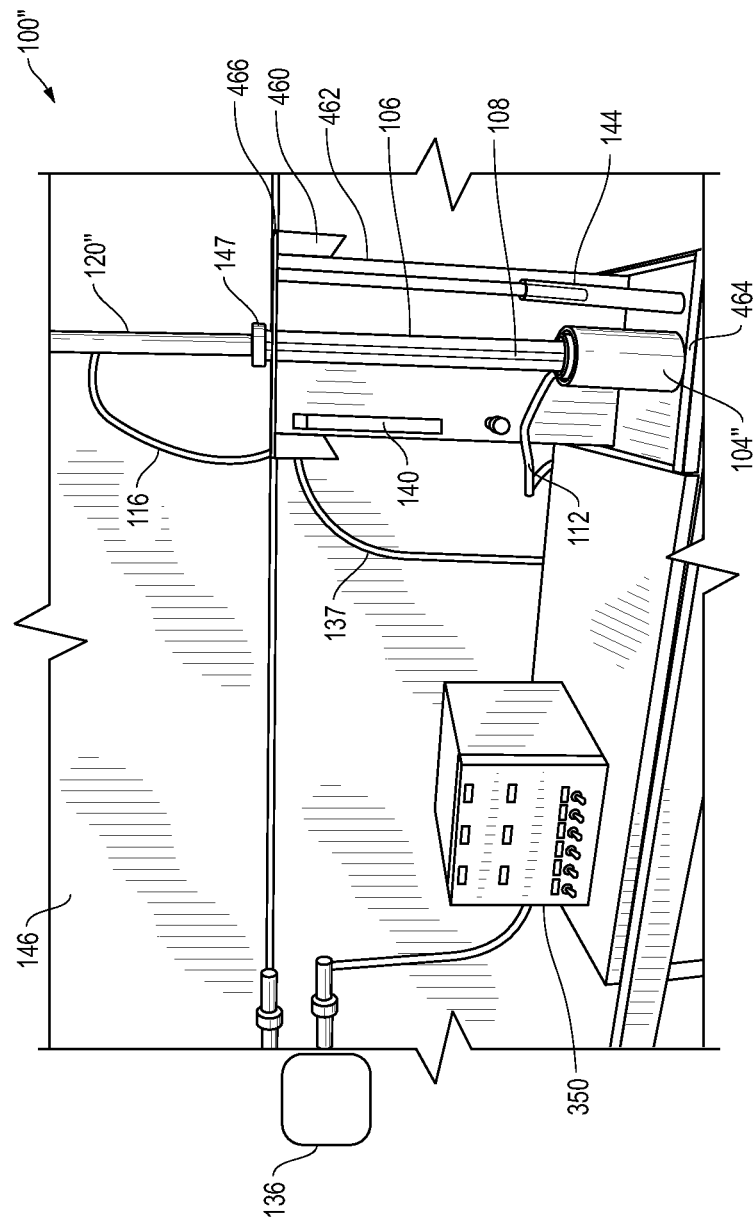
FIG. 4 is a schematic diagram depicting a single cylinder configuration of a system for testing engine lubricants in accordance with the present disclosure.

FIGS. 3 and 4 depict various configurations of a system 100' and 100", respectively. The system 100' of FIG. 3 is a multiple test system depicted in an example configuration. The system 100' includes the same components as previously described in the system 100 of FIG. 1, except that the block 104' has a plurality of cavities 110 for receiving multiple test cylinders 108 with corresponding pistons 106. Flowlines 137 are linked to lids 147 of the cylinders 108 for passing the 136 gas therein (the gas 136 is not shown in this view; see FIG. 1). A single motor 120' hydraulically operates all of the pistons 106.

As shown, the block 104 is a multi-cell aluminum block hosting six cylinders 108 for testing therein. The block 104 is mounted on a base 360 which supports the system 100'. The base 360 is positioned in hood 146. In a given example, the block 104 may include a multi-cell (e.g., 12 cell) aluminum block heater for hosting multiple cylinders 106.

The system 100' may also be provided with additional options, such as gauges 348 for monitoring pressures, and a controller 350 usable, for example, as one or more of the controllers 114, 118, 124, 132, 138, 140 of FIG. 1 for controlling various operations of the system 100'. As shown, the controller 350 is coupled to the motor 120', but could be coupled to one or more components of the system 100'. A processor 145 may also be coupled to the controller 350 for data collection and analysis. The controller may be used to selectively operate testing of one or more of the cylinders 106. The test cylinders 108 may be tested using the same or different lubricant mix 102' at the same or different temperatures, and at the same or different test cycles.

The system 100" of FIG. 4 a single test system in an example configuration. The system 100" includes the same components as previously described in the system 100 of FIG. 1, except that the block 104" is a cylindrical cup for receiving the tube 106 and a single motor 120" is provided to operate the piston 106. The motor 120" is a hydraulic cylinder for selectively extending and retracting the piston 106. Coil 116 is positioned adjacent the motor 120" for heating the piston 106. Gas 136 is injected into the cylinder 108 through lid 147 via flowline 137.

The block 104" is mounted on a base 460 with a vertical support 462 and upper and lower horizontal supports 464, 466 for the system 100". The block 104" is supported on the base 460, and the cylinder 108 is supported in the block 104" by vertical and horizontal supports 462, 464, 466. The base 460 is positioned in hood 146.

Controller 350 is coupled to various components of the system 100" for controlling operation thereof. Heating coil 112 of block 104" and heating coil 116 of piston 106 are operatively connected to the controller 350 for operation thereby. The flowline 137 is also operatively linked to the controller 350 for controlled release of gas 136 into the cylinder 108.

The testing conditions may be adjusted by selectively adjusting the lubricant mix 102' and/or the flow of gas 136. Validations may be performed using reference oils with known piston deposit performance. By way of example, commercial oils with a given confidence level (e.g., three Sequence IIIG reference oils plus one high performance IIIG oil) may be used to 'tune' the laboratory testing conditions.

As shown in FIGS. 5A-5D, correlations may be established between tests performed using the system 100 and other known test results. Examples of standards that may be used for correlations include Oil Ring Land Deposits (ORLD) and Weighted Piston Deposits (WPD). Merit rating correlations or deposit weight correlations may be determined as depicted in these figures. The reference oils used may have established repeatability confidence ranges to provide assurance in determining correlations. Test parameters may be adjusted to other engine conditions if appropriate reference oils are available.

Figure 5A:
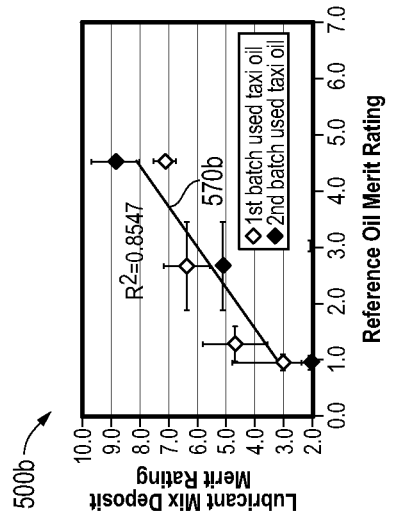
FIGS. 5A-5D are graphs depicting comparisons of test results with reference oils.

FIG. 5A is a graph 500a depicting deposit merit rating of a test lubricant mix (e.g., 102' of FIG. 1) (y-axis) versus a reference oil x-axis). In this example, the reference oil is a Three Sequence IIIG reference oils plus one high performance IIIG oil using Weighted Piston Deposit (WPD). Two batches are run using taxi oil. A best fit line 570a is generated through the collected data points. In this case, the resulting merit rating $R^2$ is 0.8004.

Figure 5B:
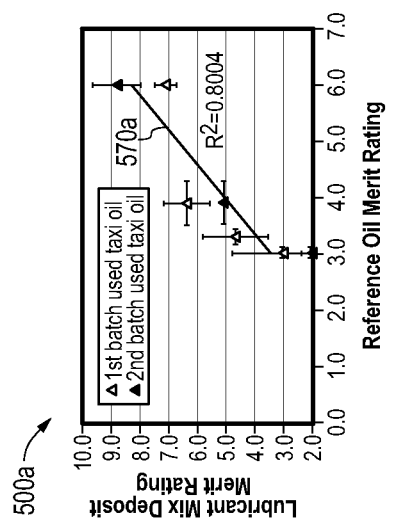

FIG. 5B is a graph 500b depicting a deposit merit rating of the test lubricant mix (y-axis) versus a reference oil x-axis). In this example, the reference oil was a Three Sequence IIIG reference oils plus one high performance IIIG oil using Oil Ring Land Deposits (ORLD). Two batches are run using taxi oil. A best fit line 570b is generated through the collected data points. In this case, the resulting merit rating $R^2$ is 0.8547.

Figure 5C:
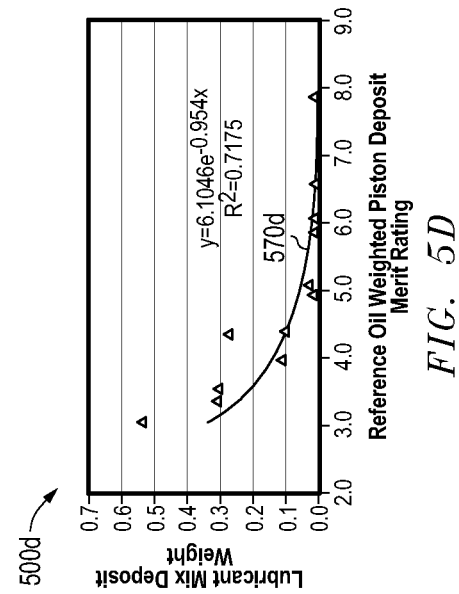

FIG. 5C is a graph 500c depicting a deposit merit rating of a reference oil x-axis) versus the test lubricant mix (y-axis). In this example, the reference oil was a Three Sequence IIIG reference oils plus one high performance IIIG oil using WPD. Two batches are run using taxi oil. A best fit line 570c is generated through the collected data points. In this case, the resulting merit rating $R^2$ is 0.7757.

Figure 5D:
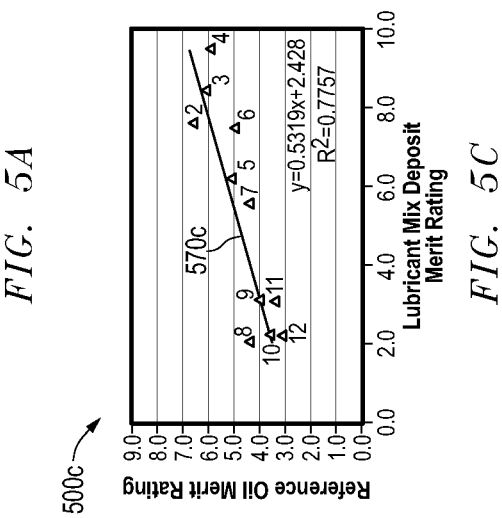

FIG. 5D is a graph 500d depicting a deposit merit rating of the test lubricant mix (y-axis) versus a reference oil x-axis). In this example, the reference oil is a Three Sequence IIIG reference oils plus one high performance IIIG oil using WPD. A best fit curve 570d is generated through the collected data points. In this case, the resulting merit rating $R^2$ is 0.7175.

Depending on the desired correlation, the graphs may be used as a tool to validate the test system and/or the lubricant mix. Based on the results of the correlations, the system, lubricant mix and/or the test cycle, adjustments may be made to enhance the test.

Figure 6:
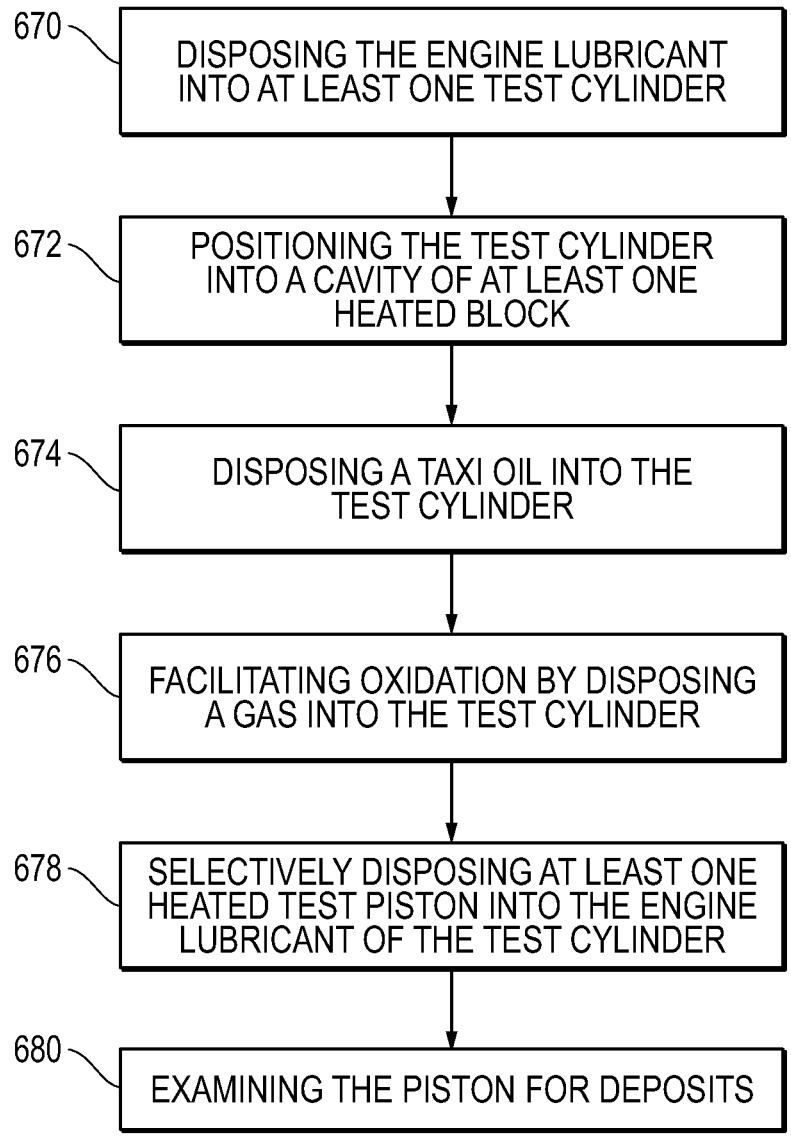
FIG. 6 is a flow chart depicting a method for testing engine lubricants in accordance with the present disclosure.

FIG. 6 depicts a method 600 of testing an engine lubricant. The method involves 670—disposing the engine lubricant into at least one test cylinder, 672—positioning the at least one test cylinder into a cavity of at least one heated block, 674—disposing a taxi oil into the test cylinder, 676—facilitating oxidation by disposing a gas into the test cylinder, 678—selectively disposing a at least one test piston into the engine lubricant of the test cylinder, and 680—examining the at least one test piston for deposits. The method may be repeated as desired and performed in any order.

Figure 7:
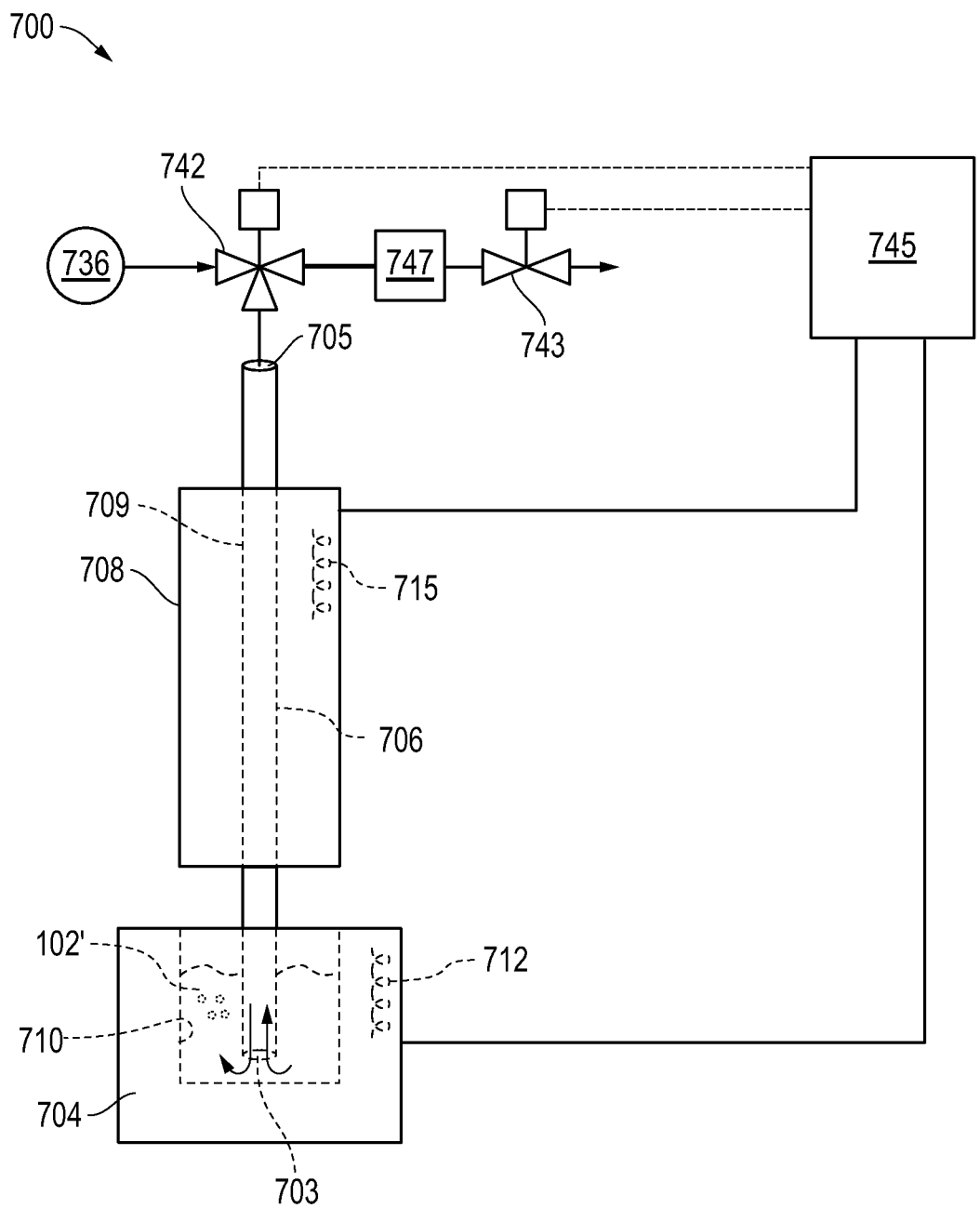
FIG. 7 is a schematic diagram depicting a gas system for testing engine lubricants in accordance with the present disclosure.

FIG. 7 depicts yet another test system 700 for simulating an engine and evaluating a lubricant, such as lubricant 102. The test system 700 includes an engine block 704, a tube 706 and a tube block 708. In this version, the lubricant 102 is part of a lubricant mix 102' positioned in the engine block 704. The tube 706 is supported above the engine block 704 and disposed into the lubricant mix 102'. The engine block 704 includes a cavity 710 for receiving the lubricant mix 102' and the tube 706. The engine block 704 also has a heated coil 712 operatively connected to a controller 745, and may operate similar to the block 104 previously described.

The tube 706 may be, for example a glass tube for the passage of fluids (e.g., gases) therethrough. A fluid end 703 of the tube 706 is positioned in cavity 710 of engine block 704. An opposite gas end 705 of the tube 706 extends above the block 704 for receiving gases therein. One or more gases 736, such as the gases 136 previously described, may be disposed through the tube 706 and into the lubricant mix 102' as previously described. The gases 736 may be linked to the tube 706 via flowlines with valve 742 for selective passage of the gases 736 therein.

The valve 742 may also be linked to a vacuum chamber 747 for selectively applying a vacuum to the tube 706. The vacuum chamber 747 may be coupled to a valve 743 and the controller 745 for selectively activating the vacuum chamber 747. The valves 742 and 743 may be selectively activated by controller 745 to dispose gases 736 into or to apply a vacuum to the tube 706. The selective control of the valves 742 and/or 743 may be used to selectively move the gases 736 into and out of the lubricant mix 102'. The movement of the fluid through the tube 706 may be used to facilitate mixing of the lubricant mix 102'.

The tube block 708 is positioned above the engine block 704 and about the tube 706 between the fluid end 703 and the gas end 705 of the tube 706. The tube block 708 may be a tubular member with a channel 709 therethrough for receiving the tube 706. The tube block 708 may be affixed to the tube 706 and supported therewith, or supported by an external support. The tube block 708 may be the same as the engine block 704 with a coil 715 therein operatively connected to controller 745 for selective heating. The engine block 704 is selectively heated by the controller 745. The engine block 704 may have a temperature that is lower than a temperature of the tube block 708. By way of example, the engine block 704 may have a temperature of about 160 C and the tube block 708 may have a temperature of about 300 C.

In operation, the tube 706 is used to selectively blow gas 736 through the tube 706 and into the lubricant mix 102' as indicated by the downward arrow. The tube 706 is heated by the tube block 708 to simulate the temperature of an engine piston. The lubricant mix 102' is heated by engine block 704 to a temperature to simulate an oil pan. Flow of gas 736 may be selectively stopped with valve 742. The valve 742 may also be selectively activated (e.g., by controller 745) to apply a vacuum from vacuum chamber 747 to pull the lubricant mix 102' into the tube 706 as indicated by the upward arrow. As test lubricant 102' is pulled into the tube 706, a film of the test lubricant 102' remains along the test lubricant 102' together with oil deposits. The tube 706 may be analyzed (e.g., weighed) to determine the amount of deposit formed thereon.

Figure 8:
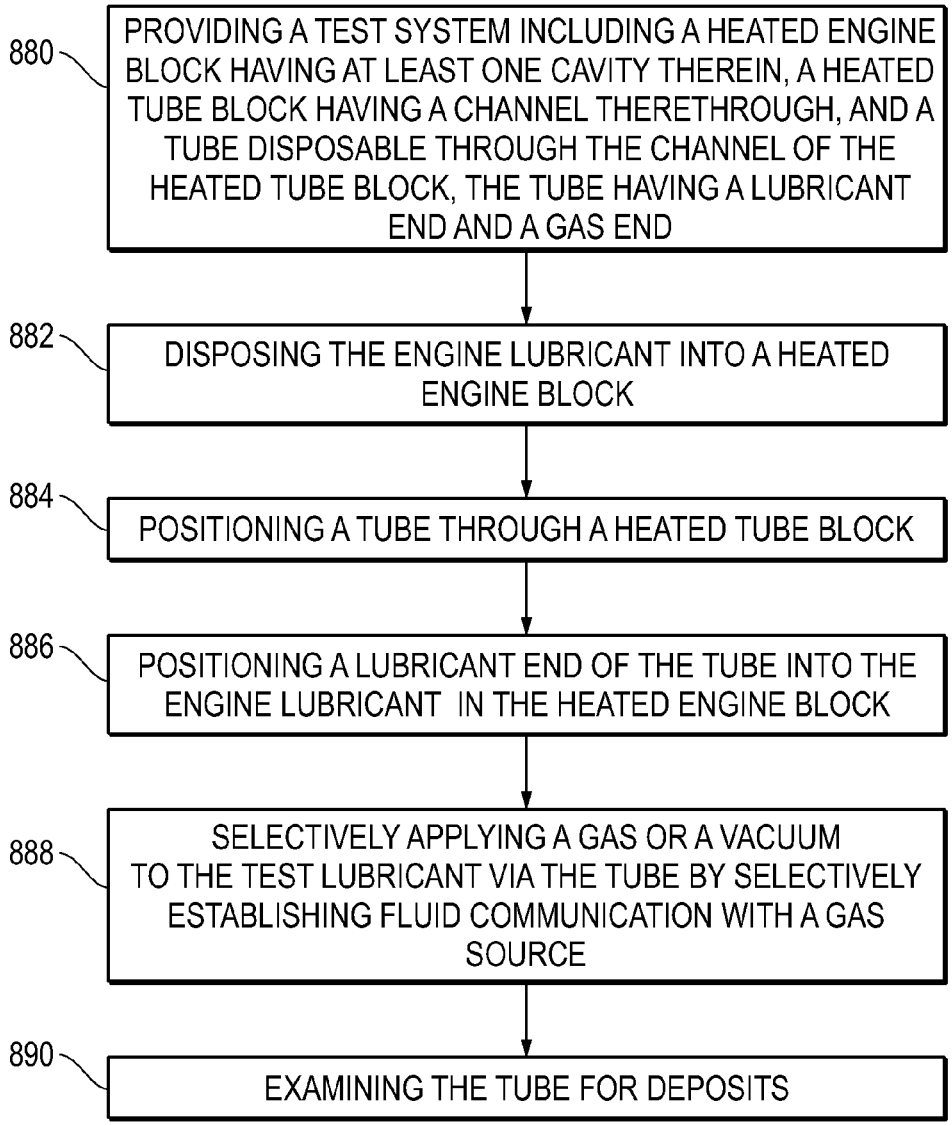
FIG. 8 is a flow chart depicting another method for testing engine lubricants in accordance with the present disclosure.

FIG. 8 depicts a method 800 of testing an engine lubricant. The method involves 880—providing a test system including a heated engine block having at least one cavity therein, a heated tube block having a channel therethrough, and a tube disposable through the channel of the heated tube block (the tube having a lubricant end and a gas end). The method also involves 882—disposing the engine lubricant into a heated engine block, 884—positioning a tube through a heated tube block, 886—positioning a lubricant end of the tube into the engine lubricant in the heated engine block, 888—selectively applying a gas or a vacuum to the test lubricant via the tube by selectively establishing fluid communication with a gas source, and 890—examining the tube for deposits.

The selectively applying may involve applying gas to the test lubricant via the test tube or applying vacuum to the test lubricant via the test tube. The method may be performed in any order, and repeated as desired.

While the embodiments are described with reference to various implementations and exploitations, it will be understood that these embodiments are illustrative and that the scope of the inventive subject matter is not limited to them. Many variations, modifications, additions and improvements are possible. For example, one or more test cylinders may be positioned in one or more test blocks, and one or more lubricants and gases disposed in the test cylinders for testing over a desired test cycle. In another example, features of the various systems may be interchanged to provide the desired overall system.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A system comprising:
    a block comprising at least one cavity therein, wherein the block is configured to be selectively heated by a block heat source;
    at least one cylinder positionable in the at least one cavity of the block, wherein the at least one cylinder is configured to receive a lubricant;
    at least one piston, wherein the at least one piston is configured to be selectively heated by a piston heat source, and configured to be selectively submerged into and retracted from the lubricant in the at least one cylinder; and
    a motor operatively connected to the at least one piston.

2. The system of claim 1, further comprising a gas disposable into the at least one cylinder whereby oxidation of the lubricant is facilitated.

3. The system of claim 2, wherein the gas comprises air, nitrogen dioxide or a combination thereof.

4. The system of claim 1, further comprising a rod operatively connecting the motor to the at least one piston.

5. The system of claim 1, further comprising at least one controller operatively connected to the block heat source, the piston heat source, the motor or a combination thereof.

6. The system of claim 1, wherein the lubricant is a lubricant mix comprising a taxi oil and a gas.

7. The system of claim 1, further comprising a vent hood.

8. The system of claim 5, further comprising a processor operatively connected to the at least one controller.

9. A method comprising:
    providing a lubricant;
    providing a system comprising:
        a block comprising at least one cavity therein, wherein the block is configured to be selectively heated by a block heat source;
        at least one cylinder positionable in the at least one cavity of the block, wherein the at least one cylinder is configured to receive the lubricant;
        at least one piston, wherein the at least one piston is configured to be selectively heated by a piston heat source, and configured to be selectively submerged into and retracted from the lubricant in the at least one cylinder; and
        a motor operatively connected to the at least one piston;
    disposing the lubricant into the at least one cylinder;
    positioning the at least one cylinder into the cavity of the at least one block;
    selectively heating the block, the at least one piston, or both;
    selectively submerging or retracting the at least one piston into or from the lubricant; and
    examining the at least one piston for deposits.

10. The method of claim 9, further comprising disposing a gas into the at least one cylinder.

11. The method of claim 9, wherein the lubricant is a lubricant mix comprising a taxi oil and a gas.

12. A system comprising:
    a block comprising a cavity therein, wherein the cavity is configured to receive a lubricant, and wherein the block is configured to be selectively heated by a block heat source;
    a tube block comprising a channel therethrough, wherein the tube block is configured to be selectivity heated by a tube block heat source;

a tube disposable through the channel of the tube block, wherein the tube comprises a lubricant end configured to be disposed in the lubricant in the at least one cavity and a gas end configured to receive a gas; and a gas source in selective fluid communication with the gas end of the tube, wherein the gas source is configured to allow selective passage of the gas through the tube, to selectively apply a vacuum to the tube, or both.

13. The system of claim 12, wherein the gas source is configured to allow selective passage of the gas through the tube and to selectively apply a vacuum to the tube.

14. The system of claim 12, wherein the gas comprises at least one gas selected from the group consisting of: air, nitrogen dioxide and a combination thereof.

15. The system of claim 12, further comprising at least one valve operatively connected to the gas source and the tube to allow selective passage of the gas through the tube, to selectively apply a vacuum to the tube, or both.

16. The system of claim 15, further comprising a controller operatively connected to the at least one valve for selective activation thereof.

17. The system of claim 12, wherein at least one of the block heat source, the tube block heat source or both comprises a heat coil.

18. The system of claim 12, further comprising at least one controller operatively connected to the block, the tube block, the gas source, or a combination thereof.

19. The system of claim 12, wherein the lubricant is a lubricant mix comprising a taxi oil and a gas.

20. A method comprising:
providing a lubricant;
providing a system comprising:
   a block comprising a cavity therein, wherein the cavity is configured to receive the lubricant, and wherein the block is configured to be selectively heated by a block heat source;
   a tube block comprising a channel therethrough, wherein the tube block is configured to be selectivity heated by a tube block heat source;
   a tube disposable through the channel of the tube block, wherein the tube comprises a lubricant end configured to be disposed in the lubricant in the at least one cavity and a gas end configured to receive a gas; and;
   a gas source in selective fluid communication with the gas end of the tube, wherein the gas source is configured to supply the gas to the gas end of the tube and allow selective passage of the gas through the tube, to selectively apply a vacuum to the tube, or a combination thereof;
disposing the lubricant into the cavity of the block;
positioning the tube through the tube block;
positioning the lubricant end of the tube into the lubricant;
selectively heating the block, the tube, or both;
supplying the gas to the gas end of the tube and selectively allowing passage of the gas through the tube;
selectively applying a vacuum to the tube so as to draw at least a portion of the lubricant into the tube via the lubricant end of the tube; and
examining the tube for deposits.

21. The system of claim 1, wherein at least one of the block heat source, the tube block heat source or both comprises a heat coil.

22. The system of claim 8, further comprising at least one sensor operatively connected to the processor, wherein the at least one sensor is configured to provide data for at least one testing parameter selected from piston temperature, block temperature, piston position and a combination thereof.

23. The method of claim 9, wherein the system further comprises at least one controller operatively connected to the block heat source, the piston heat source, the motor or a combination thereof.

24. The method of claim 20, wherein both the block and the tube are heated and wherein the block has a temperature that is less than a temperature of the tube block.

25. The method of claim 20, wherein the system further comprises at least one controller operatively connected to the block heat source, the tube block heat source, the gas source or a combination thereof.

26. The method of claim 20, wherein the system further comprises at least one valve operatively connected to the gas source and the tube to allow selective passage of the gas through the tube, to selectively apply a vacuum to the tube, or both.

* * * * *